US011623908B2

(12) United States Patent
Schulte, II et al.

(10) Patent No.: US 11,623,908 B2
(45) Date of Patent: Apr. 11, 2023

(54) METHOD FOR PURIFICATION OF A BIPHENOL TETRAACID COMPOSITION AND A BIPHENOL TETRAACID COMPOSITION

(71) Applicant: SHPP GLOBAL TECHNOLOGIES B.V., Bergen op Zoom (NL)

(72) Inventors: James Patrick Schulte, II, Mt. Vernon, IN (US); Juan Justino Rodriguez Ordonez, Cartagena (ES)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/417,960

(22) PCT Filed: Jan. 30, 2020

(86) PCT No.: PCT/US2020/015777
§ 371 (c)(1),
(2) Date: Jun. 24, 2021

(87) PCT Pub. No.: WO2020/160201
PCT Pub. Date: Aug. 6, 2020

(65) Prior Publication Data
US 2022/0073445 A1   Mar. 10, 2022

(30) Foreign Application Priority Data
Jan. 31, 2019   (EP) .................................... 19382065

(51) Int. Cl.
*C07C 51/47*   (2006.01)
*C07C 63/331*   (2006.01)
*C07C 51/42*   (2006.01)

(52) U.S. Cl.
CPC .............. *C07C 51/47* (2013.01); *C07C 51/42* (2013.01); *C07C 63/331* (2013.01)

(58) Field of Classification Search
CPC ......... C07C 51/02; C07C 51/42; C07C 51/47; C07C 63/331; C07C 65/24
See application file for complete search history.

(56) References Cited

U.S. PATENT DOCUMENTS

| 3,879,428 A | 4/1975 | Heath et al. |
| 3,905,942 A | 9/1975 | Takekoshi et al. |
| 3,956,320 A | 5/1976 | Heath et al. |
| 4,293,683 A | 10/1981 | Takekoshi et al. |
| 4,324,882 A | 4/1982 | Takekoshi |
| 4,808,731 A | 2/1989 | Berdahl et al. |
| 5,434,240 A | 7/1995 | Eastmond et al. |
| 6,727,370 B1 | 4/2004 | Brunelle et al. |
| 7,495,113 B2 | 2/2009 | Pressman et al. |
| 2006/0066004 A1 | 3/2006 | Richards et al. |
| 2007/0073035 A1 | 3/2007 | Stella et al. |

FOREIGN PATENT DOCUMENTS

| CN | 101402625 A | 4/2009 | |
| CN | 101696199 | 4/2010 | |
| CN | 106279085 | 1/2017 | |
| EP | 0413415 A1 | 2/1991 | |
| EP | 0593200 A1 | 4/1994 | |
| JP | H04149149 A | 5/1992 | |
| JP | H04334346 A | 11/1992 | |
| JP | 2011195466 A | 10/2011 | |
| WO | WO-9941222 A1 * | 8/1999 | ............. C07C 51/43 |
| WO | 2017172593 A1 | 10/2017 | |

OTHER PUBLICATIONS

International Search Report for the corresponding International Application No. PCT/US2020/015777 International Filing Date: Jan. 30, 2020; dated May 4, 2020; 5 pages.
Takekoshi, T. et al., "Polyetherimides. I. Preparation of Dianhydrides Containing Aromatic Ether Groups", Journal of Polymer Science: Polymer Chemistry Edition, vol. 23, 1985; pp. 1759-1769.
Takekoshi, T. et al., "Polyetherimides. II. High-Temperature Solution Polymerization", Journal of Polymer Science: Polymer Symposium, vol. 74, 1986; pp. 93-108.
Written Opinion for the corresponding International Application No. PCT/US2020/015777; International Filing Date: Jan. 30, 2020; dated May 4, 2020; 12 pages.
Zhao, N. et al., "3,3'-[Biphenyl-4,4'-diylbis(oxy)]-diphthalic acid," Organic Compounds, Acta Cryst., E68, 2012; 8 pages.

* cited by examiner

*Primary Examiner* — Yate' K Cutliff

(74) *Attorney, Agent, or Firm* — Cantor Colburn LLP

(57) ABSTRACT

A method for purification of a biphenol tetraacid composition includes contacting the biphenol tetraacid composition with a solvent including a C1-6 alcohol to form a slurry and isolating the purified biphenol tetraacid from the slurry. The biphenol tetraacid composition includes a biphenol tetraacid and a biphenol. A purified biphenol tetraacid composition is also described.

13 Claims, No Drawings

METHOD FOR PURIFICATION OF A BIPHENOL TETRAACID COMPOSITION AND A BIPHENOL TETRAACID COMPOSITION

CROSS REFERENCE TO RELATED APPLICATIONS

This application is a National Stage application of PCT/US2020/015777, filed Jan. 30, 2020, which claims the benefit of European patent application number 19382065.1, filed Jan. 31, 2019, both of which are hereby incorporated by reference in their entirety.

BACKGROUND

Poly(imides), and poly(etherimides) (PEI), are high performance polymers having a glass transition temperature (Tg) of greater 180° C. These polymers further have high strength, heat resistance, and modulus, and broad chemical resistance. Poly(etherimides) are widely used in applications as diverse as automotive and electrical/electronic applications since these compositions offer good mechanical and thermal properties.

Poly(etherimides) can be prepared by condensation polymerization, for example of a dianhydride with a diamine. In order to obtain good reaction kinetics, achieve high molecular weight, and provide a stable, processable polymer product, high purity monomer components are desirable. Additionally, some applications can require that the polymers have good optical clarity, and good thermal and mechanical properties. The level of haze exhibited by an article can be related to the method by which the polymer is prepared.

Suitable dianhydrides can be prepared through a ring-closing process of an aromatic tetraacid. It can be difficult to provide the desired aromatic tetraacids that have high purity (e.g., are free of residual alkali metals and their salts) using known processes. It is also common for biphenolic contaminants to be present in the tetraacid precursors. Thus, there remains a need in the art for an improved process for the preparation of aromatic tetraacids, in particular those derived from biphenol, in order to ultimately provide poly (etherimides) with low levels of contaminants and improved properties such as low haze, high optical clarity, good reaction kinetics, and high molecular weight.

SUMMARY

A method for purification of a biphenol tetraacid composition comprising a biphenol tetraacid of the formula

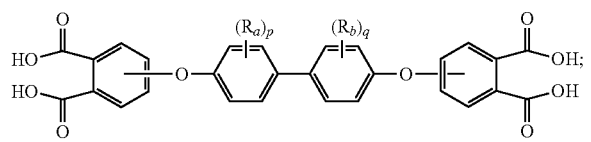

and
a biphenol of the formula

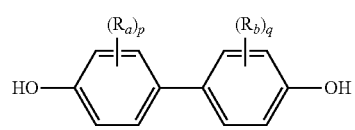

wherein in the foregoing formulas $R^a$ and $R^b$ are each independently a halogen or a monovalent $C_{1-6}$ alkyl group and p and q are each independently an integer of 0 to 4; comprises: contacting the biphenol tetraacid composition with a solvent comprising a $C_{1-6}$ alcohol to form a slurry comprising the biphenol tetraacid composition; and isolating a purified biphenol tetraacid from the slurry, wherein isolating the purified biphenol tetraacid comprises filtering the slurry to provide a wet cake comprising the biphenol tetraacid, and washing the wet cake with additional solvent comprising the $C_{1-6}$ alcohol, water, an organic solvent miscible with the $C_{1-6}$ alcohol, or a combination thereof.

A biphenol tetraacid composition comprising a biphenol tetraacid of the formula

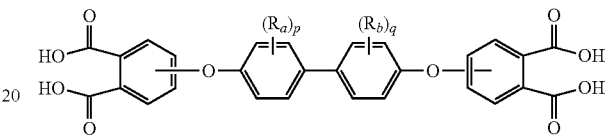

wherein $R^a$ and $R^b$ are each independently a halogen or a monovalent $C_{1-6}$ alkyl group and p and q are each independently an integer of 0 to 4; and greater than 0 to less than 1 weight percent, preferably greater than 0 to less than 0.7 weight percent, more preferably greater than 0 to less than 0.2 weight percent, even more preferably greater than 0 to less than 0.16 weight percent of the biphenol, as determined by ultra performance liquid chromatography; greater than 0 to less than 10 ppm of sodium ions; greater than 0 to less than 50 ppm total of sodium ions, potassium ions, calcium ions, zinc ions, aluminum ions, titanium ions, iron ions, and phosphorus ions; greater than 0 to less than 250 ppm of sulfate ions; and greater than 0 to less than 3,000 ppm total of phosphate ions, sulfate ions, and chloride ions.

The above described and other features are exemplified by the following detailed description.

DETAILED DESCRIPTION

The present inventors have unexpectedly discovered that aromatic biphenol tetraacids can be prepared having low levels of impurities using a new methodology. The aromatic biphenol tetraacids can be particularly useful for forming the corresponding dianhydrides as poly(etherimide) precursors.

Accordingly, an aspect of the present disclosure is a method for purification of a biphenol tetraacid composition. The biphenol tetraacid composition comprises a biphenol tetraacid of the formula

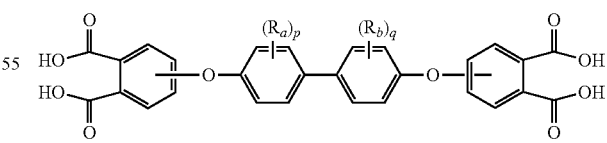

wherein $R^a$ and $R^b$ are each independently a halogen or a monovalent $C_{1-6}$ alkyl group and p and q are each independently an integer of 0 to 4, preferably wherein p and q are each 0. In some embodiments, p, q, or both can be 1 to 4, preferably 1 to 2, more preferably 1. In some embodiments, $R^a$ and $R^b$ can each independently be a $C_{1-3}$ alkyl group, for example a methyl group. The divalent bonds of the biphenol group can be in the 3,3' position, the 3,4' position, or the 4,4' position. In some embodiments, the biphenol tetraacid can be an isomer mixture. For example, 10 to 100 weight percent of the biphenol tetraacid can have the divalent bonds of the biphenol group in the 3,3' position, or 90 to 100 weight percent of the biphenol tetraacid can have the divalent bonds of the biphenol group in the 3,3' position. Preferably, the divalent bonds of the biphenol group can be in the 3,3' position. In a specific embodiment, the biphenol can be of the formula

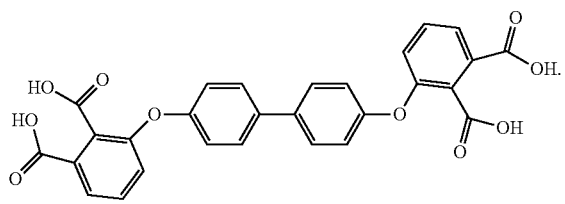

The biphenol tetraacid can be prepared from an aromatic bisimide precursor. The N-organo-substituted aromatic bisimide can be hydrolyzed in a caustic process to produce a biphenol tetraacid salt which can then be acidified (e.g., with a mineral acid) to produce the biphenol tetraacid having the above formula. This route to provide the tetraacids requires the base hydrolysis of the aromatic bisimide and conversion of the resulting salt to the acid. Inorganic salts can be generated by this process, which can contaminate the biphenol tetraacid. Thus in addition to the biphenol tetraacid, the biphenol tetraacid composition can optionally further include one or more of a sodium ion, potassium ion, calcium ion, zinc ion, aluminum ion, titanium ion, iron ion, phosphorus ion, phosphate ion, sulfate ion, chloride ion, or a combination thereof. The foregoing ionic species can be present in the biphenol tetraacid composition in an amount of 0 to 1700 ppm, or 0 to 1000 ppm, or greater than 0 to 1700 ppm, or greater than 0 to 1000 ppm based on the total weight of the biphenol tetraacid composition.

In addition to the biphenol tetraacid and when present, the one or more ionic species, the biphenol tetraacid composition comprises a biphenol of the formula

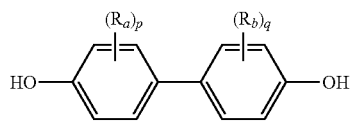

wherein $R^a$, $R^b$, p and q are as defined above. In an embodiment, p and q are each 0. The biphenol can be present in the composition in an amount of 1 to 10 weight percent, or 1 to 5 weight percent, or 1 to 3 weight percent, each based on the total weight of the biphenol tetraacid composition.

The method for purifying the biphenol tetraacid composition comprises contacting the biphenol tetraacid composition with a solvent comprising a $C_{1-6}$ alcohol to form a slurry. In some embodiments, the $C_{1-6}$ alcohol comprises isopropanol, ethylene glycol, methanol, ethanol, n-propanol, butanol, or a combination thereof. In an embodiment, the $C_{1-6}$ alcohol comprises isopropanol, ethylene glycol, or a combination thereof. In a specific embodiment, the $C_{1-6}$ alcohol comprises isopropanol. The solvent can exclude any solvent other than the $C_{1-6}$ alcohol. In some embodiments, the solvent, can optionally further comprise water or an organic solvent that is miscible with the $C_{1-6}$ alcohol. The organic solvent can comprise, for example, ortho-dichlorobenzene, para-dichlorobenzene, meta-dichlorobenzene, chlorobenzene, toluene, benzene, xylene, 1,2,4-trichlorobenzene, 1,3,4-trichlorobenzene, preferably ortho-dichlorobenzene. In a specific embodiment, the solvent comprises the $C_{1-6}$ alcohol and water, preferably isopropanol and water. The $C_{1-6}$ alcohol and the water can be used in a weight ratio of water:isopropanol of 0.25:1 to 5:1, or 0.5:1 to 4:1, or 0.5:1 to 2.5:1, or 0.5:1 to 2:1, or 0.5:1 to 1.5:1. In yet another specific embodiment, the biphenol tetraacid can be further washed by the $C_{1-6}$ alcohol, preferably isopropanol. The solvent can be present in a weight ratio of solvent to biphenol tetraacid of 0.65:1 to 4:1.

In some embodiments the slurry formed from the solvent and the biphenol tetraacid composition can be agitated. Agitation can be for a time of 10 minutes to 2 hours, or 30 minutes to 2 hours, or 1 to 2 hours, or greater than 30 minutes, or greater than 30 minutes to 5 hours, or 45 minutes to 5 hours, or 1 hour to 5 hours. Agitation can be, for example, at a speed of 50 rpm or greater, preferably 150 rpm or greater. The slurry can be formed, maintained, and optionally agitated at a temperature of 15 to 80° C., or 15 to 70° C., or 15 to 50° C., or 15 to 30° C., or 20 to 30° C. In a specific embodiment, the slurry is formed and agitated at ambient temperature.

The method further comprises isolating a purified biphenol tetraacid from the slurry. Isolating the purified biphenol tetraacid from the slurry can generally be by any solid-liquid separation technique. For example, the isolating can be by filtering, centrifugation, and the like, or a combination thereof. In an embodiment, the method can comprise isolating the purified biphenol tetraacid by filtration to provide a wet cake comprising the purified biphenol tetraacid, and optionally, further washing the wet cake with additional solvent. The additional solvent can comprise the $C_{1-6}$ alcohol, water, the miscible organic solvent, or a combination thereof.

Advantageously, no additional purification steps are necessary to provide the purified biphenol tetraacid. For example, the method can exclude additional purification steps, such as recrystallization, in particular recrystallization from corrosive solvents, such as acetic acid or acetic anhydride.

The purified biphenol tetraacid composition can advantageously comprise reduced amounts of residual impurities. For example, the purified biphenol tetraacid composition comprises less than 1 weight percent, preferably less than 0.7 weight percent, more preferably less than 0.2 weight percent, even more preferably less than 0.16 weight percent of the biphenol, as determined by ultra performance liquid chromatography (UPLC), as further described in the working examples below. The purified biphenol tetraacid composition can comprise less than 10 ppm of sodium ions. The purified biphenol tetraacid composition can comprise less than 50 ppm total of sodium ions, potassium ions, calcium ions, zinc ions, aluminum ions, titanium ions, iron ions, and phosphorus ions. The purified biphenol tetraacid composition can comprise less than 250 ppm of sulfate ions. The purified biphenol tetraacid composition can comprise less than 3,000 ppm total of phosphate ions, sulfate ions, and chloride ions.

A purified biphenol tetraacid composition represents another aspect of the present disclosure. The biphenol tetraacid composition comprises a biphenol tetraacid of the formula

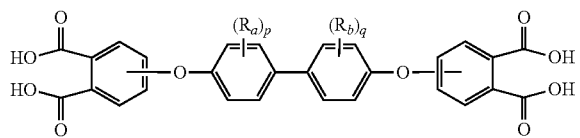

wherein $R^a$, $R^b$, p, and q can be as defined above. In a specific embodiment, p and q are each 0. The divalent bonds of the biphenol group can be in the 3,3' position, the 3,4' position, or the 4,4' position. In some embodiments, the biphenol tetraacid can be an isomer mixture. For example, 10 to 100 weight percent of the biphenol tetraacid can have the divalent bonds of the biphenol group in the 3,3' position, or 90 to 100 weight percent of the biphenol tetraacid can have the divalent bonds of the biphenol group in the 3,3' position. Preferably, the divalent bonds of the biphenol group can be in the 3,3' position. In a specific embodiment, the biphenol can be of the formula

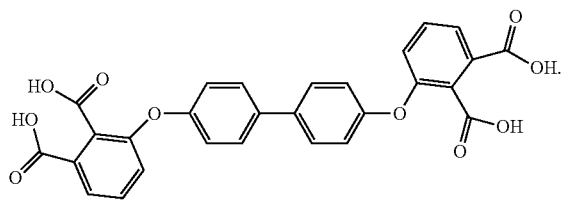 [SMILES: O=C(O)c1cccc(Oc2ccc(-c3ccc(Oc4cccc(C(=O)O)c4C(=O)O)cc3)cc2)c1C(=O)O]

The purified biphenol tetraacid composition comprises less than 1 weight percent, preferably less than 0.7 weight percent, more preferably less than 0.2 weight percent, even more preferably less than 0.16 weight percent of the biphenol, as determined by ultra performance liquid chromatography (UPLC); less than 10 ppm of sodium ions; less than 50 ppm total of sodium ions, potassium ions, calcium ions, zinc ions, aluminum ions, titanium ions, iron ions, and phosphorus ions; less than 250 ppm of sulfate ions; and less than 3,000 ppm total of phosphate ions, sulfate ions, and chloride ions. In an aspect, the purified biphenol tetraacid composition can comprise greater than 0 to less than 1 weight percent, preferably greater than 0 to less than 0.7 weight percent, more preferably greater than 0 to less than 0.2 weight percent, even more preferably greater than 0 to less than 0.16 weight percent of the biphenol, as determined by ultra performance liquid chromatography; greater than 0 to less than 10 ppm of sodium ions; greater than 0 to less than 50 ppm total of sodium ions, potassium ions, calcium ions, zinc ions, aluminum ions, titanium ions, iron ions, and phosphorus ions; greater than 0 to less than 250 ppm of sulfate ions; and greater than 0 to less than 3,000 ppm total of phosphate ions, sulfate ions, and chloride ions.

The present inventors have therefore provided an improved process for the preparation of high purity biphenol tetraacids. The purified biphenol tetraacids of the present disclosure have significantly reduced levels of inorganic salts as well as organic biphenolic impurities. The biphenol tetraacids of the present disclosure can be particularly well suited for the preparation of high purity poly(etherimides) having a desirable combination of properties, including good optical clarity, high heat performance, low water uptake, good mechanical properties and improved flow at high shear.

This disclosure is further illustrated by the following examples, which are non-limiting.

EXAMPLES

Materials used in the following Examples are described in Table 1.

TABLE 1

| Material | Chemical Description |
| --- | --- |
| 3,3'-BPoTA | 3,3'-biphenol diphthalic acid (3,3'-biphenol tetraacid) |
| |  |
| 3,4'-BPoTA | 3,4'-biphenol diphthalic acid (3,4'-biphenol tetraacid) |
| |  |

TABLE 1-continued

| Material | Chemical Description |
|---|---|
| 4,4'-BPoTA | 4,4'-biphenol diphthalic acid (4,4'-biphenol tetraacid) 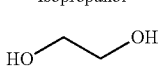 |
| DI Water | Deionized water |
| IPA | Isopropanol |
| Ethylene glycol | HO–CH₂–CH₂–OH |
| o-DCB | 1,2-dichlorobenzene |

In the following Examples 1-31 a biphenol tetraacid (BPoTA) having 95.2-96.8 weight % of 3,3'-BPoTA and 3,4'-BPoTA (combined, based on the total weight of the BPoTA composition) and 3.2-4.8 weight % of biphenol was treated with different alcohols, mixtures of alcohol and water, and mixtures of alcohol and o-DCB under different conditions of temperature, time, and solids content. The composition of the BPoTA composition was determined by UPLC.

Ultra-performance liquid chromatography (UPLC) analyses in the following examples were performed on a Waters ACQUITY UPLC BEH C18 1.7 μm 2.1×50 mm column at 35° C. PDA detection was performed at 232 nm with a flow rate of 0.313 mL/min. A gradient method was used with a dual solvent system of acetonitrile and acidic water (4 L DI $H_2O+3$ mL 85% $H_3PO_4$).

All residual levels of metals (sodium, potassium, zinc, calcium, aluminum, iron, titanium, phosphorus) in the following examples are determined by an inductively coupled plasma-digestion (ICP-Dig) method which uses an ICP spectrometer equipped with: an axial and/or radial viewing, a Gem Cone and/or Ultrasonic nebulizer, and a microwave digestion system equipped with appropriate sample digestion vessels set. Samples are prepared using concentrated nitric acid, hydrochloric acid, sulfuric acid, and/or hydrofluoric acid—supra pure grades.

Residual levels of anions (sulfates, chlorides, phosphates, nitrates, nitrites) present in BPoTA samples were measured by total ion chromatography combustion (IC-Total) using a calibrated Dionex ICS 2000 instrument.

The following Examples 1-6 used a starting BPoTA composition including sodium (69 ppm), potassium (27 ppm), zinc (1 ppm), calcium (5 ppm), aluminum (3 ppm), iron (3 ppm), titanium (0 ppm), phosphorus (6 ppm), as determined by an ICP digest method; sulfates (949 ppm), chlorides (591 ppm), phosphates (<20 ppm), as determined by IC-Totals method; and 92.93 mol % (95.87 wt %) BPoTA isomers; 6.36 mol % (3.83 wt %) biphenol, as determined by UPLC at 254 nm.

Examples 7-13 used a BPoTA composition of 93.98 mol % BPoTA isomers (95.72 wt %); 5.31 mol % (3.20 wt %) biphenol, as determined by HPLC at 232 nm and 254 nm.

Comparative Example 1

A 500 mL beaker with mechanical stirrer was charged with IPA (200 g) and then agitated at 175 rpm. The BPoTA composition (27.28 g, 27.0 g dry mass, 96.34% purity, 50.57 mmol) was then added portion-wise over 2-4 minutes. The mixture was allowed to agitate for 60 minutes at ambient temperature. Next, the slurry was filtered through a medium-fritted glass funnel. No washing of the cake was performed. The orange filtrate was discarded, and the solids were dried further in a vacuum (0.4 inches Hg) oven at 60-70° C. overnight to provide 25.01 g of a white solid in 96.1% yield. UPLC: 97.23 mol % BPoTA isomers; 1.26 mol % (0.67 wt %) biphenol.

Example 2

A 500 mL beaker with mechanical stirrer was charged with IPA (63 g) and then agitated at 175 rpm. The BPoTA composition (27.28 g, 27.0 g dry mass, 96.34% purity, 50.57 mmol) was then added portion-wise over 2-4 minutes. The mixture was allowed to agitate for 60 minutes at ambient temperature. Next, the slurry was filtered through a medium-fritted glass funnel. The cake was washed with IPA (50 g) at ambient temperature without agitation. The orange filtrate was discarded, and the solids were dried further in a vacuum (0.4 inches Hg) oven at 60-70° C. overnight to provide 25.11 g of a white solid in 96.5% yield. UPLC: 98.11 mol % BPoTA isomers; 0.49 mol % (0.26 wt %) biphenol.

Example 3

A 500 mL beaker with mechanical stirrer was charged with IPA (78 g) and then agitated at 175 rpm. The BPoTA composition (27.28 g, 27.0 g dry mass, 96.34% purity, 50.57 mmol) was then added portion-wise over 2-4 three minutes. The mixture was allowed to agitate for 60 minutes at ambient temperature. Next, the slurry was filtered through a medium-fritted glass funnel. The cake was washed with IPA (50 g) at ambient temperature without agitation. The orange filtrate was discarded and the solids were dried further in a vacuum (0.4 inches Hg) oven at 60-70° C. overnight to provide 25.15 g of a white solid in 96.7% yield. UPLC: 98.34 mol % BPoTA isomers; 0.19 mol % (0.10 wt %) biphenol.

Example 4

A 500 mL beaker with mechanical stirrer was charged with IPA (78 g) and then agitated at 175 rpm. The BPoTA composition (27.28 g, 27.0 g dry mass, 96.34% purity, 50.57 mmol) was then added portion-wise over 2-4 minutes. The mixture was allowed to agitate for 60 minutes at ambient temperature. Next, the slurry was filtered through a medium-fritted glass funnel. The cake was washed with deionized water (50 g) at ambient temperature without agitation. The orange filtrate was discarded, and the solids were dried further in a vacuum (0.4 inches Hg) oven at 60-70° C. overnight to provide 25.08 g of a white solid in 96.4% yield. UPLC: 98.31 mol % BPoTA isomers; 0.27 mol % (0.15 wt %) biphenol.

Comparative Example 5

A 500 mL beaker with mechanical stirrer was charged with IPA (78 g) and then agitated at 175 rpm. The BPoTA composition (27.28 g, 27.0 g dry mass, 96.34% purity, 50.57 mmol) was then added portion-wise over 2-4 minutes. The mixture was allowed to agitate for 30 minutes at ambient temperature. Next, the slurry was filtered through a medium-fritted glass funnel. The cake was washed with IPA (50 g) at ambient temperature without agitation. The orange filtrate was discarded, and the solids were dried further in a vacuum (0.4 inches Hg) oven at 60-70° C. overnight to provide 25.04 g of a white solid in 96.3% yield. UPLC: 97.53 mol % BPoTA isomers; 0.83 mol % (0.44 wt %) biphenol.

Comparative Example 6

A 500 mL beaker with mechanical stirrer was charged with IPA (78 g) and then agitated at 175 rpm. The BPoTA composition (27.28 g, 27.0 g dry mass, 96.34% purity, 50.57 mmol) was then added portion-wise over 2-4 minutes. The mixture was allowed to agitate for 60 minutes at ambient temperature. Next, the slurry was filtered through a medium-fritted glass funnel. No washing of the cake was performed. The orange filtrate was discarded, and the solids were dried further in a vacuum (0.4 inches Hg) oven at 60-70° C. overnight to provide 25.5 g of a white solid in 98.0% yield. UPLC: 97.18 mol % BPoTA isomers; 1.27 mol % (0.68 wt %) biphenol.

Example 7

A 250 mL beaker with magnetic stir bar was charged with BPoTA powder (6.0 g) and 15 g of isopropanol (IPA) were added. The mixture was agitated at 25° C. using a stir plate. After one hour, the mixture was filtered under vacuum through a Buchner funnel using 2 micrometer filtration paper. The solids were washed with IPA (4 g) then dried further in a vacuum oven at 90° C. overnight to provide 5.7 g of a white solid containing 102 ppm (0.0102 wt %) of biphenol.

Example 8

A 250 mL beaker with magnetic stir bar was charged with BPoTA powder (12.0 g) and 15 g of IPA were added. The mixture was agitated at 25° C. using a stir plate. After one hour, the mixture was filtered under vacuum through a Buchner funnel using 2 micrometer filtration paper. The solids were washed with IPA (8 g) then were dried further in a vacuum oven at 90° C. overnight to provide 11.1 g of a white solid containing 203 ppm (0.0203 wt %) of biphenol.

Example 9

A 250 mL beaker with magnetic stir bar was charged with BPoTA powder (12.0 g) and 10 g of IPA were added. The mixture was agitated at 25° C. using a stir plate. After one hour, the mixture was filtered under vacuum through a Buchner funnel using 2 micrometer filtration paper. The solids were washed with IPA (8 g) then were dried further in a vacuum oven at 90° C. overnight to provide 11.4 g of a white solid containing 265 ppm (0.0265 wt %) of biphenol.

Example 10

A 250 mL beaker with magnetic stir bar was charged with BPoTA powder (50.0 g) and 50 g of IPA were added. The mixture was agitated at 25° C. using a stir plate. After one hour, the mixture was filtered under vacuum through a Buchner funnel using 2 micrometer filtration paper. The solids were washed with IPA (33 g) then were dried further in a vacuum oven at 90° C. overnight to provide 47.3 g of a white solid containing 486 ppm (0.0486 wt %) of biphenol.

Example 11

A vessel was charged with 3,3'-BPoTA wet cake (150 kg, 70 wt % solids, 4.42 wt % biphenol (dry weight basis), 195 mol) and then inerted with nitrogen. Next, IPA (246 kg) was charged into the vessel and the vent valve was closed. Agitation was slowly brought to 80% power and then continued for two hours at ambient temperature.

Meanwhile, DI water was connected to a 40-liter Nutsche filter via a flex hose. After the two hours of agitation, a TEFLON-lined flexible hose and fittings with the appropriate compatible material of construction were used to transfer the 3,3'-BPoTA/IPA slurry from the vessel to the Nutsche filter, containing a 60 micrometer TEFLON filter media. Under 50 psig, the liquid was separated from the solids in the Nutsche filter and the filtrate was sent into a carbon steel drum, which was tied into the vent header. After the filtration was completed, the transfer process was repeated until the product cake filled the bottom section of the Nutsche filter. The filter was then depressurized to ambient pressure.

Next, additional fresh IPA (10-12 kg) was added to the Nutsche filter to wash the product cake. As before, the system was pressurized, and the filtrate was sent into a carbon steel drum. The filter was then depressurized to ambient pressure. At this point, a representative sample of the 3,3'-BPoTA cake was sampled and analyzed for the presence of biphenol by UPLC. When present, additional IPA (8 kg) was used to wash the cake again.

A hold tank was cleaned and filled with DI water and then pressurized to 50 psig at ambient temperature. Water (10 kg) was then transferred from the hold tank to the Nutsche filter to wash the product cake with no soak time. As before, the system was pressurized, and the filtrate was sent into a polypropylene tote. The combined aqueous waste was neutralized immediately to pH of 6-9. This isolation process was repeated multiple times until all material from the vessel was collected. The wet cakes were transferred into foil pans and dried in a vacuum oven at 90-105° C. under nitrogen until dry. A total dry weight of 14.41 kg was collected of pure product to provide a yield of 14.35% for this trial.

The purified sample had the following composition: sodium (12 ppm), potassium (7.6 ppm), zinc (0 ppm), calcium (5.8 ppm), aluminum (1.8 ppm), iron (2.9 ppm), titanium (0 ppm), phosphorus (8.3 ppm), as determined by an ICP digest method; sulfates (42 ppm), chlorides (334 ppm), phosphates (<20 ppm), as determined by IC-Totals method; and 98.8 mol % BPoTA isomers, 0 mol % biphenol, as determined by UPLC.

Example 12

A 250 mL beaker with magnetic stir bar was charged with BPoTA wet cake (25.0 g, 67% solids, 33% water) and 125 g of IPA were added. The mixture was heated and agitated at 70° C. using a stir plate. After 3 hours, the mixture was filtered under vacuum through a Buchner funnel using 2-micron filtration paper. The solids were washed with IPA (11 g) then were dried further in a vacuum oven at 90° C. overnight to provide 10.85 g of a white solid containing 41 ppm (0.0041 wt %) of biphenol.

Example 13

A 250 mL beaker with magnetic stir bar was charged with BPoTA wet cake (20.0 g, 67% solids, 33% water) and 50 g of IPA were added. The mixture was heated and agitated at 70° C. using a stir plate. After 3 hours, the mixture was filtered under vacuum through a Buchner funnel using 2-micron filtration paper. The solids were washed with IPA (9 g) then were dried further in a vacuum oven at 90° C. overnight to provide 10.5 g of a white solid containing 50 ppm (0.0050 wt %) of biphenol.

Example 14

A 250 mL beaker with magnetic stir bar was charged with BPoTA wet cake (20.0 g, 67% solids, 33% water) and 50 g of IPA were added. The mixture was heated and agitated at 70° C. using a stir plate. After 1 hours, the mixture was filtered under vacuum through a Buchner funnel using 2-micrometer filtration paper. The solids were washed with IPA (9 g) then were dried further in a vacuum oven at 90° C. overnight to provide 11.4 g of a white solid containing 72 ppm (0.0072 wt %) of biphenol.

Table 2 below summarizes the conditions used for examples 1-14. Triturations were performed at ambient temperature with an agitation rate of 175 rpm prior to filtration for examples 1 to 11, versus triturations at 70° C. for examples 12 to 14.

TABLE 2

| Example | Dry wt crude BPoTA | IPA | IPA/BPoTA (mass/mass) | Agitation Temp (° C.) | Agitation time | Final wash conditions |
|---|---|---|---|---|---|---|
| 1* | 27.0 g | 200 g | 7.4:1 | 25° C. | 60 min | NONE |
| 2 | 27.0 g | 63 g | 2.33:1 | 25° C. | 60 min | 50 g IPA |
| 3 | 27.0 g | 78 g | 2.89:1 | 25° C. | 60 min | 50 g IPA |
| 4 | 27.0 g | 78 g | 2.89:1 | 25° C. | 60 min | 50 g H$_2$O |
| 5* | 27.0 g | 78 g | 2.89:1 | 25° C. | 30 min | 50 g IPA |
| 6* | 27.0 g | 78 g | 2.89:1 | 25° C. | 60 min | NONE |
| 7 | 6 g | 15 g | 2.50:1 | 25° C. | 60 min | 4 g IPA |
| 8 | 12 g | 15 g | 1.25:1 | 25° C. | 60 min | 8 g IPA |
| 9 | 12 g | 10 g | 0.83:1 | 25° C. | 60 min | 8 g IPA |
| 10 | 50 g | 50 | 1:1 | 25° C. | 60 min | 33 g IPA |
| 11 | 105 g | 246 g | 2.34:1 | 25° C. | 4 hours | IPA then H$_2$O |
| 12 | 16.75 g | 125 g | 7.46:1 | 70° C. | 3 hours | 11 g IPA |
| 13 | 13.4 g | 50 g | 3.73:1 | 70° C. | 3 hours | 9 g IPA |
| 14 | 13.4 g | 50 g | 3.73:1 | 70° C. | 60 min | 9 g IPA |

*Denotes comparative examples

Table 3 shows the results from the IPA trituration studies for examples 1-14. In the cases where the triturations were performed at ambient temperature (examples 1-11), the recovered yield was greater than 92%, except on large scale (example 11). For cases where the triturations were performed at 70° C. (examples 12-14), the recovered yield was significantly reduced. Results show that BPoTA cakes which were not washed after filtration from the IPA trituration solvent (Examples 1 and 6) resulted in product with 0.76 wt % biphenol present. When larger amounts of IPA were used (Example 3 versus Example 2) in the trituration of the BPoTA, the product purity was improved. Furthermore, washing the wet cake with water (Example 4) resulted in product with higher amounts of biphenol present than when washing with IPA (Example 3), but lower amounts of sodium were present. Also, trituration of the wet cake for only 30 minutes (Example 5) resulted in product with higher amounts of biphenol present than when triturating for 60 minutes (Example 3).

Examples 7, 8, 9, and 10 exhibited very low amounts of residual biphenol and recovered yields were high (>92%). Examples 9 and 10 used ratios of IPA:BPoTA were 0.83 and 1, respectively. Experiments 12, 13 and 14 demonstrated that by increasing washing temperature, very low levels of residual biphenol can be achieved consistently but at reduced yield.

TABLE 3

| | Initial | | | | Final | | | | | | | | |
|---|---|---|---|---|---|---|---|---|---|---|---|---|---|
| Ex. | mol % BPoTA isomers | wt % BPoTA isomers | mol % biphenol | wt % biphenol | mol % BPoTA isomers | wt % BPoTA isomers | mol % biphenol | wt % biphenol | Sodium (ppm) | Sulfates (ppm) | Phosphates (ppm) | Chlorides (ppm) | Yield (%) |
| 1* | 92.93% | 95.87% | 6.36% | 3.83% | 97.23% | 99.04% | 1.26% | 0.76% | 52 | 594 | <20 | 434 | 96.2 |
| 2 | 92.93% | 95.87% | 6.36% | 3.83% | 98.11% | 99.50% | 0.49% | 0.30% | 66 | 802 | <20 | 447 | 96.5 |
| 3 | 92.93% | 95.87% | 6.36% | 3.83% | 98.34% | 99.69% | 0.19% | 0.11% | 42 | 774 | <20 | 383 | 96.7 |
| 4 | 92.93% | 95.87% | 6.36% | 3.83% | 98.31% | 99.64% | 0.27% | 0.16% | 8 | 217 | <20 | 429 | 96.4 |
| 5* | 92.93% | 95.87% | 6.36% | 3.83% | 97.53% | 99.30% | 0.83% | 0.50% | 36 | 672 | <20 | 411 | 96.3 |
| 6* | 92.93% | 95.87% | 6.36% | 3.83% | 97.18% | 99.04% | 1.27% | 0.76% | 41 | 655 | <20 | 376 | 98.0 |
| 7 | 93.98% | 96.50% | 5.31% | 3.20% | 99.51% | 99.79% | 0.02% | 0.01% | <10 | <50 | — | — | 95.0 |
| 8 | 93.98% | 96.50% | 5.31% | 3.20% | 99.49% | 99.78% | 0.03% | 0.02% | <10 | <50 | — | — | 92.5 |
| 9 | 93.98% | 96.50% | 5.31% | 3.20% | 99.48% | 99.77% | 0.04% | 0.03% | <10 | <50 | — | — | 95.0 |
| 10 | 93.98% | 96.50% | 5.31% | 3.20% | 99.44% | 99.75% | 0.08% | 0.05% | <10 | <50 | — | — | 94.6 |
| 11 | 90.10% | 95.28% | 8.36% | 4.42% | 98.80% | 99.80% | 0% | 0% | 12 | 42 | <20 | 334 | 14.4 |
| 12 | 93.98% | 96.50% | 5.31% | 3.20% | 99.52% | 99.80% | 0.01% | 0.00% | <10 | <50 | — | — | 64.8 |
| 13 | 93.98% | 96.50% | 5.31% | 3.20% | 99.52% | 99.80% | 0.01% | 0.01% | <10 | <50 | — | — | 78.4 |
| 14 | 93.98% | 96.50% | 5.31% | 3.20% | 99.51% | 99.79% | 0.01% | 0.01% | <10 | <50 | — | — | 85.1 |

*Denotes comparative examples

The following Examples 15-27 demonstrate trituration of BPoTA with water/IPA mixtures. Examples 15-19 used BPoTA with a composition comprised sodium (69 ppm), potassium (27 ppm), zinc (1 ppm), calcium (5 ppm), aluminum (3 ppm), iron (3 ppm), titanium (0 ppm), phosphorus (6 ppm), as determined by an ICP digest method; sulfates (949 ppm), chlorides (591 ppm), phosphates (<20 ppm), as determined by IC-Totals method; and 92.93 mol % (95.87 wt %) BPoTA isomers; 6.36 mol % (3.83 wt %) biphenol, as determined by UPLC.

Examples 20-24 used BPoTA having a composition of 93.98 mol % BPoTA isomers (96.50 wt %); 5.31 mol % (3.20 wt %) biphenol. Example 25 used BPoTA with a composition of 91.30 mol % BPoTA isomers (94.89 wt %); 7.99 mol % (4.81 wt %) biphenol. Examples 26-27 used BPoTA with a composition of 91.98 mol % BPoTA isomers (95.30 wt %); 7.31 mol % (4.40 wt %) biphenol as determined by HPLC.

Example 15

A 500 mL beaker with mechanical stirrer was charged with DI water (52.02 g) and then agitated at 175 rpm. The BPoTA composition (27.28 g, 27.0 g dry mass, 96.34% purity, 50.57 mmol) was then added portion-wise over 2-4 minutes. Next, IPA (26 g) was added and the mixture was allowed to agitate for 60 minutes at ambient temperature. The slurry was filtered through a medium-fritted glass funnel. The cake was washed with IPA (36 g) at ambient temperature without agitation. The orange filtrate was discarded, and the solids were dried further in a vacuum (0.4 inches Hg) oven at 60-70° C. overnight to provide 25.51 g of a white solid in 98.1% yield. UPLC: 98.28 mol % BPoTA isomers; 0.10 mol % (0.06 wt %) biphenol.

Example 16

A 500 mL beaker with mechanical stirrer was charged with DI water (70.2 g) and then agitated at 175 rpm. The BPoTA composition (27.28 g, 27.0 g dry mass, 96.34% purity, 50.57 mmol) was then added portion-wise over 2-4 minutes. Next, IPA (35.1 g) was added and the mixture was allowed to agitate for 60 minutes at ambient temperature. The slurry was filtered through a medium-fritted glass funnel. The cake was washed with IPA (36 g) at ambient temperature without agitation. The orange filtrate was discarded, and the solids were dried further in a vacuum (0.4 inches Hg) oven at 60-70° C. overnight to provide 25.20 g of a white solid in 96.9% yield. UPLC: 98.33 mol % BPoTA isomers; 0.18 mol % (0.10 wt %) biphenol.

Example 17

A 500 mL beaker with mechanical stirrer was charged with DI water (84.24 g) and then agitated at 175 rpm. The BPoTA composition (27.28 g, 27.0 g dry mass, 96.34% purity, 50.57 mmol) was then added portion-wise over three minutes. Next, IPA (21.06 g) was added and the mixture was allowed to agitate for 60 minutes at ambient temperature. The slurry was filtered through a medium-fritted glass funnel. The cake was washed with IPA (50 g) at ambient temperature without agitation. The orange filtrate was discarded, and the solids were dried further in a vacuum (0.4 inches Hg) oven at 60-70° C. overnight to provide 25.37 g of a white solid in 97.5% yield. UPLC: 98.17 mol % BPoTA isomers; 0.22 mol % (0.12 wt %) biphenol.

Example 18

A 500 mL beaker with mechanical stirrer was charged with DI water (70.2 g) and then agitated at 175 rpm. The BPoTA composition (27.28 g, 27.0 g dry mass, 96.34% purity, 50.57 mmol) was then added portion-wise over 2-4 minutes. Next, IPA (35.1 g) was added and the mixture was allowed to agitate for 60 minutes at ambient temperature. The slurry was filtered through a medium-fritted glass funnel. The cake was washed with IPA (59 g) at ambient temperature without agitation. The orange filtrate was discarded, and the solids were dried further in a vacuum (0.4 inches Hg) oven at 60-70° C. overnight to provide 25.53 g of a white solid in 98.2% yield. UPLC: 98.29 mol % BPoTA isomers; 0.14 mol % (0.08 wt %) biphenol.

Example 19

A 500 mL beaker with mechanical stirrer was charged with deionized water (52.65 g) and then agitated at 175 rpm. The BPoTA composition (27.28 g, 27.0 g dry mass, 96.34% purity, 50.57 mmol) was then added portion-wise over 2-4 minutes. Next, IPA (52.65 g) was added and the mixture was allowed to agitate for 60 minutes at ambient temperature. The slurry was filtered through a medium-fritted glass funnel. The cake was washed with IPA (59 g) at ambient temperature without agitation. The orange filtrate was discarded, and the solids were dried further in a vacuum (0.4 inches Hg) oven at 60-70° C. overnight to provide 24.95 g of a white solid in 95.9% yield. UPLC: 98.67 mol % BPoTA isomers; 0.0 mol % (0.0 wt %) biphenol.

Example 20

A 250 mL beaker with magnetic stir bar was charged with BPoTA powder (12.0 g) and 8 g of IPA and 4 g DI water were added. The mixture was agitated at 25° C. using a stir plate. After one hour, the mixture was filtered under vacuum through a Buchner funnel using 2-micron filtration paper. The solids were washed with IPA/H$_2$O (2:1, 8 g) then were dried further in a vacuum oven at 90° C. overnight to provide 11.3 g of a white solid containing 791 (0.0791 wt %) ppm of biphenol.

Example 21

A repeat of Example 20 was completed yielding 11.2 g of white BPoTA powder with 862 ppm (0.0862 wt %) biphenol.

Example 22

A 250 mL beaker with magnetic stir bar was charged with BPoTA powder (12.0 g) and 6 g of IPA and 6 g DI water were added. The mixture was agitated at 25° C. using a stir plate. After one hour, the mixture was filtered under vacuum through a Buchner funnel using 2-micron filtration paper. The solids were washed with IPA/H$_2$O (1:1, 8 g) then were dried further in a vacuum oven at 90° C. overnight to provide 11.3 g of a white solid containing 632 ppm (0.0632 wt %) of biphenol.

Example 23

A repeat of Example 22 was completed yielding 11.7 g of white BPoTA powder with 498 ppm (0.0498 wt %) biphenol.

Example 24

A 250 mL beaker with magnetic stir bar was charged with BPoTA powder (50.0 g) and 25 g of IPA and 25 g DI water were added. The mixture was agitated at 25° C. using a stir plate. After one hour, the mixture was filtered under vacuum through a Buchner funnel using 2-micron filtration paper. The solids were washed with IPA/H$_2$O (1:1, 33 g) then were dried further in a vacuum oven at 90° C. overnight to provide 47.7 g of a white solid containing 661 ppm (0.0661 wt %) of biphenol.

Example 25

A vessel was charged with DI water (194 kg) and agitated at 100% power. Next, 3,3'-BPoTA wet cake (140 kg, 53.85 wt % solids, 4.81 wt % biphenol (dry weight basis), 139 mol) was charged and then the vessel was inerted with nitrogen. Next, IPA (122 kg) was charged into the vessel and the vent valve was closed. Agitation at 100% power was continued for 2.5-3 hours at ambient temperature.

Meanwhile, DI water was connected to a 40-liter Nutsche filter via a flex hose. After the 2.5-3 hours of agitation, a Teflon-lined flexible hose and fittings with the appropriate compatible material of construction were used to transfer the milky H$_2$O/3,3'-BPoTA/IPA slurry from the vessel to the 40-liter Nutsche filter, containing a 60-micron Teflon® filter media. Under 50 psig, the liquid was separated from the solids in the Nutsche filter and the filtrate was sent into a carbon steel drum, which was tied into the vent header. After the filtration was completed, the transfer process was repeated until the product cake filled the bottom section of the Nutsche filter. The filter was then depressurized to ambient pressure.

Next, additional fresh IPA (7-9 kg) was added to the Nutsche filter to wash the product cake. As before, the system was pressurized, and the filtrate was sent into a carbon steel drum. The filter was then depressurized to ambient pressure. At this point, a representative sample of the 3,3'-BPoTA cake was sampled with a column tube and analyzed for the presence of biphenol by UPLC. When present, additional IPA (8 kg) was used to wash the cake again.

A hold tank was cleaned and filled with DI water and then pressurized to 50 psig at ambient temperature. Water (10 kg) was then transferred from the hold tank to the Nutsche filter to wash the product cake. As before, the system was pressurized, and the filtrate was sent into a polypropylene tote. The combined aqueous waste was neutralized immediately to pH of 6-9. This isolation process was repeated multiple times until all material from the vessel was collected. A total of six cakes were collected then transferred into foil pans and dried in a vacuum oven at 90-105° C. under nitrogen until dry. A total dry weight of 61.47 kg was collected of pure product to provide a yield of 85.7% for this trial.

The purified sample had the following composition: sodium (10 ppm), potassium (15 ppm), zinc (0 ppm), calcium (5 ppm), aluminum (0 ppm), iron (4 ppm), titanium (0 ppm), phosphorus (9 ppm), as determined by an ICP digest method; sulfates (<20 ppm), phosphates (22 ppm), chlorides (316 ppm), as determined by IC-Totals method; and 98.0 mol % BPA-TA isomers, 0 mol % biphenol, as determined by UPLC.

Example 26

A pilot plant unit consisting of two vessels, a Nutsche filter and nitrogen inlets was used to perform Comparative Example 30. A total of 2892 pounds (lbs) of RO (reverse osmosis) water was charged to the first vessel. Then 1446 lbs of BPoTA wet cake containing 66.07% solids (water to balance) and 4.4 weight % biphenol (dry basis vs. cake solids) was charged to the first vessel. Finally, 2892 lbs of IPA was charged to the first vessel and mixture was agitated at 25° C. for four hours. Then the first vessel bottom was recycled to the Nutsche filter and pumped off the Nutsche back to the first vessel. Once the solution looks clear, solvent was pumped off Nutsche to the second vessel. Once all the solvent was removed, the cake was washed with o-DCB passing through the filter to remove the IPA entrained in the cake. Analysis of the cake showed 66.03% solids and 0.03 weight % (300 ppm) biphenol present (dry basis vs. cake solids).

Example 27

A pilot plant unit consisting of two vessels, a Nutsche filter and nitrogen inlets (graph attached) was used to perform Comparative Example 31. A total of 3314 lbs of RO (reverse osmosis) water was charged to the first vessel. Then 1657 lbs of BPoTA wet cake containing 66.07% solids (water to balance) and 4.4 weight % biphenol (dry basis vs. cake solids) was charged to the first vessel. Finally, 3314 lbs of IPA was charged to the first vessel and mixture was agitated at 25° C. during four hours. Then the first vessel bottom was recycled to the Nutsche filter and pumped off the Nutsche back to the first vessel. Once the solution looked clear, solvent was pumped off Nutsche to the second vessel. Once all the solvent was off, the cake was washed with o-DCB passing through the filter to remove the IPA entrained in the cake. Analysis of the cake showed 51.02% solids and 0.03 weight % (300 ppm) biphenol present (dry basis vs. cake solids).

Table 4 below summarizes the conditions used for Examples 15-27, where a mixture of IPA with water was used to triturate the crude BPoTA which contained 3.20-4.81 wt % biphenol and greater than 69 ppm of sodium. Triturations were performed at ambient temperature with an agitation rate of 175 rpm prior to filtration. Subsequent washing of the BPoTA cakes was also performed in Examples 15-27.

TABLE 4

| Example | Dry wt crude BPoTA | H₂O | IPA | HO/IPA | solvent/BPoTA (m/m) | Agitation time | wash conditions |
|---|---|---|---|---|---|---|---|
| 15 | 27.0 g | 52.02 g | 26 g | 2:1 | 2.89:1 | 60 min | 36 g IPA |
| 16 | 27.0 g | 70.2 g | 35.1 g | 2:1 | 3.9:1 | 60 min | 36 g IPA |
| 17 | 27.0 g | 84.24 g | 21.06 g | 4:1 | 3.9:1 | 60 min | 50 g IPA |
| 18 | 27.0 g | 70.2 g | 35.1 g | 2:1 | 3.9:1 | 60 min | 59 g IPA |
| 19 | 27.0 g | 52.65 g | 52.65 g | 1:1 | 3.9:1 | 60 min | 59 g IPA |
| 20 | 12 g | 4 g | 8 g | 0.5:1 | 1:1 | 60 min | IPA/H₂O |
| 21 | 12 g | 4 g | 8 g | 0.5:1 | 1:1 | 60 min | IPA/H₂O |
| 22 | 12 g | 6 g | 6 g | 1:1 | 1:1 | 60 min | IPA/H₂O |
| 23 | 12 g | 6 g | 6 g | 1:1 | 1:1 | 60 min | IPA/H₂O |
| 24 | 50 g | 25 g | 25 g | 1:1 | 1:1 | 3 hrs | IPA then H₂O |
| 25 | 75.39 g | 258.61 g | 122 g | 2.12:1 | 5.05:1 | 2 hrs | IPA then H₂O |
| 26 | 955 lbs | 3383 lbs | 2892 lbs | 1.17:1 | 6.57:1 | 4 hrs | o-DCB |
| 27 | 1095 lbs | 3876 lbs | 3314 lbs | 1.17:1 | 6.57:1 | 60 min | IPA/H₂O |

Table 5 shows the results from the H₂O/IPA trituration studies of Examples 15-27. In most cases the recovered yield was greater than 93% and the amount of sodium in the final and using a chlorinated solvent to remove the entrained solvents also leads to BPoTA of high purity and low sodium content.

TABLE 5

| | Initial | | | | Final | | | | | | | | |
|---|---|---|---|---|---|---|---|---|---|---|---|---|---|
| Ex. | mol % BPoTA isomers | wt % BPoTA isomers | mol % biphenol | wt % biphenol | mol % BPoTA isomers | wt % BPoTA isomers | mol % biphenol | wt % biphenol | Sodium (ppm) | Sulfates (ppm) | Phosphates (ppm) | Chlorides (ppm) | Yield (%) |
| 15 | 92.93% | 95.87% | 6.36% | 3.83% | 98.28% | 99.74% | 0.10% | 0.06% | 4 | 186 | <20 | 405 | 98.1 |
| 16 | 92.93% | 95.87% | 6.36% | 3.83% | 98.33% | 99.69% | 0.18% | 0.11% | 3 | 27 | <20 | 369 | 96.9 |
| 17 | 92.93% | 95.87% | 6.36% | 3.83% | 98.17% | 99.67% | 0.22% | 0.13% | 2 | 47 | <20 | 418 | 97.5 |
| 18 | 92.93% | 95.87% | 6.36% | 3.83% | 98.29% | 99.72% | 0.14% | 0.08% | 2 | 49 | <20 | 426 | 98.2 |
| 19 | 92.93% | 95.87% | 6.36% | 3.83% | 98.67% | 99.80% | 0% | 0% | 1 | 51 | <20 | 332 | 95.9 |
| 20 | 93.98% | 96.50% | 5.31% | 3.20% | 99.39% | 99.72% | 0.13% | 0.08% | <10 | <50 | — | — | 94.2 |
| 21 | 93.98% | 96.50% | 5.31% | 3.20% | 99.38% | 99.71% | 0.14% | 0.09% | <10 | <50 | — | — | 93.3 |
| 22 | 93.98% | 96.50% | 5.31% | 3.20% | 99.42% | 99.74% | 0.11% | 0.06% | <10 | <50 | — | — | 94.2 |
| 23 | 93.98% | 96.50% | 5.31% | 3.20% | 99.44% | 99.75% | 0.08% | 0.05% | <10 | <50 | — | — | 97.5 |
| 24 | 93.98% | 96.50% | 5.31% | 3.20% | 99.42% | 99.73% | 0.11% | 0.07% | <10 | <50 | — | — | 95.4 |
| 25 | 91.30% | 94.89% | 7.99% | 4.81% | 99.48% | 99.80% | 0.05% | 0.00% | <10 | — | — | — | 85.7 |
| 26 | 91.98% | 95.30% | 7.31% | 4.40% | 99.48% | 99.77% | 0.05% | 0.03% | 37 | 50-100 | — | — | >95 |
| 27 | 91.98% | 95.30% | 7.31% | 4.40% | 99.48% | 99.77% | 0.05% | 0.03% | 41 | 50-100 | — | — | >95 |

BPoTA was significantly reduced to less than 10 ppm for all but two examples. Furthermore, results show that examples 15-27 all provided product with less than 0.14 wt % biphenol present. A water to IPA ratio (mass/mass) between 0.5:1 and 4:1 was used during the trituration of the crude BPoTA. The total solvent mass to crude BPoTA mass ratio employed was between 1:1 and 6.57:1. Examples 15-23, and 27 were triturated at 175 rpm for 60 minutes in H₂O/IPA prior to filtration. The BPoTA wet cakes were subsequently washed with between 36 to 59 g of IPA, or a mixture of IPA/H₂O. In contrast, examples 24-26 were agitated for a few hours prior to filtration. The BPoTA wet cakes were subsequently washed with IPA, a mixture of IPA/H₂O, IPA then water, or o-DCB alone. Results from Example 17 shows that when higher amounts of water are used in the trituration solvent mixture, a less efficient removal of the biphenol occurs (compared to example 15). Furthermore, results from Example 18 show that using more IPA to wash the BPoTA wet cake results in slightly higher purity of the final product (compared to example 16). Examples 20-23 show that washing the BPoTA cake with a water to IPA ratio (mass/mass) 2:1 and 1:1 leads to a purified cake with low levels of residual biphenol, sodium, and sulfate contaminants. Washing the isolated BPoTA cakes with IPA, followed by water (examples 24 and 25), also led to low levels of biphenol and sodium content. Examples 26 and 27 show that washing a wet cake in a proportion 1:4 (wet cake/solvent, mass/mass)

The following Examples 28-29 demonstrate trituration of BPoTA with o-DCB/IPA mixtures. The initial BPoTA composition comprised sodium (68 ppm), potassium (31 ppm), zinc (2 ppm), calcium (9 ppm), aluminum (3 ppm), iron (5 ppm), titanium (0 ppm), phosphorus (7 ppm), as determined by an ICP digest method; sulfates (1,661 ppm), chlorides (592 ppm), phosphates (<20 ppm), as determined by IC-Totals method; and 90.24 mol % BPoTA isomers; 7.20 mol % (4.34 wt %) biphenol, as determined by UPLC.

Example 28

A 500 mL beaker with mechanical stirrer was charged with o-DCB (50 g) and then agitated at 175 rpm. The BPoTA composition (64.2 g, 35.0 g dry mass, 95.79% purity, 65.17 mmol) was then added portion-wise over 2-4 minutes. Next, IPA (50.0 g) was added and the mixture was allowed to agitate for 60 minutes at ambient temperature. The slurry was filtered through a medium-fritted glass funnel. The cake was washed with IPA (77 g) at ambient temperature without agitation. The orange filtrate was discarded, and the solids were dried further in a vacuum (0.4 inches Hg) oven at 25° C. overnight to provide 28.10 g of a white solid in 83.8% yield. UPLC: 98.94 mol % BPoTA isomers; 0.0 mol % (0.0 wt %) biphenol.

Example 29

A 500 mL beaker with mechanical stirrer was charged with o-DCB (162.8 g) and then agitated at 175 rpm. The BPoTA composition (64.2 g, 35.0 g dry mass, 95.79% purity, 65.17 mmol) was then added portion-wise over 2-4 minutes. Next, IPA (68.4 g) was added and the mixture was allowed to agitate for 60 minutes at ambient temperature. The slurry was filtered through a medium-fritted glass funnel. The cake was washed with IPA (77 g) at ambient temperature without agitation. The orange filtrate was discarded, and the solids were dried further in a vacuum (0.4 inches Hg) oven at 25° C. overnight to provide 26.43 g of a white solid in 78.8% yield. UPLC: 98.99 mol % BPoTA isomers; 0.0 mol % (0.0 wt %) biphenol.

Table 6 summarizes the conditions used for examples 28 and 29, where a mixture of IPA with o-DCB was used to triturate the crude BPoTA which contained 4.34 wt % biphenol and 68 ppm of sodium. Triturations were performed at ambient temperature with an agitation rate of 175 rpm prior to filtration. Subsequent washing of the BPoTA cakes were also performed in examples 28 and 29.

The following Examples 30-31 demonstrate trituration of BPoTA with ethylene glycol and ethylene glycol/$H_2O$ mixtures. The initial BPoTA composition comprised 93.98 mol % BPoTA isomers (95.72 wt %) and 5.31 mol % (3.20 wt %) biphenol, as determined by HPLC at 232 nm and 254 nm.

Example 30

A 250 mL beaker with magnetic stir bar was charged with BPoTA powder (12.0 g) and 12 g of ethylene glycol were added. The mixture was agitated at 25° C. using a stir plate. After one hour, the mixture was filtered under vacuum through a Buchner funnel using 2-micron filtration paper. The solids were washed with ethylene glycol (8 g) then were dried further in a vacuum oven yielding 11.3 g of a pale-yellow powder with 2,094 ppm (0.2094 wt %) of biphenol.

Comparative Example 31

A 250 mL beaker with magnetic stir bar was charged with BPoTA powder (12.0 g) and 12 g of ethylene glycol and 4 g of DI water were added. The mixture was agitated at 25° C. using a stir plate. After one hour, the mixture was filtered under vacuum through a Buchner funnel using 2-micron filtration paper. The solids were washed with ethylene glycol/$H_2O$ (3:1, 8 g) then were dried further in a vacuum oven yielding 11.6 g of a pale-yellow powder with 9,812 ppm (0.9812 wt %) of biphenol.

Table 8 shows that washing BPoTA crude powder (3.20 wt % biphenol) with glycol alone (example 30) leads to significantly reduced levels of residual biphenol (0.21 wt %). In contrast, washing the BPoTA crude powder with a glycol/water mixture (comparative example 31) leads to a BPoTA powder with still high levels (0.98 wt %) of biphenol.

TABLE 6

| Ex. | Dry wt crude BPoTA | o-DCB | IPA | o-DCB/IPA | solvent/BPoTA (m/m) | Agitation rate | Agitation time | Wash conditions |
| --- | --- | --- | --- | --- | --- | --- | --- | --- |
| 28 | 35.0 g | 50 g | 50 g | 1:1 | 2.86:1 | 175 rpm | 60 min | 77 g IPA |
| 29 | 35.0 g | 162.8 g | 68.4 g | 2.38:1 | 6.61:1 | 175 rpm | 60 min | 77 g IPA |

Table 7 shows the results from the o-DCB/IPA trituration studies of Examples 28 and 29. In these cases, the recovered yields were significantly less than in the previous studies. Results show that both examples 28 and 29 provided product with non-detectable amounts of biphenol and very low levels of sodium. An o-DCB to IPA ratio (mass/mass) between 1:1 and 2.38:1 was used during the trituration of the crude BPoTA. The total solvent mass to crude BPoTA mass ratio employed was between 2.86:1 to 6.61:1. Examples 28 and 29 were both triturated at 175 rpm for 60 minutes in o-DCB/IPA prior to filtration. The BPoTA wet cakes were subsequently washed with 77 g of IPA. Results show that using a higher ratio of solvent to crude BPoTA during trituration gives a lower yield of recovered product.

TABLE 7

| | Initial | | | Final | | | | | | | |
| --- | --- | --- | --- | --- | --- | --- | --- | --- | --- | --- | --- |
| Ex. | mol % BPoTA isomers | mol % biphenol | wt % biphenol | mol % BPoTA isomers | mol % biphenol | wt % biphenol | Sodium (ppm) | Sulfates (ppm) | Phosphates (ppm) | Chlorides (ppm) | Yield (%) |
| 28 | 90.24% | 7.20% | 4.34% | 98.84% | 0% | 0% | 2 | <20 | <20 | 2,904 | 83.79 |
| 29 | 90.24% | 7.20% | 4.34% | 98.99% | 0% | 0% | 2 | 75 | <20 | 1,969 | 78.81 |

TABLE 8

| Example | BPoTA crude powder | solvent | solvent composition | solvent/BPoTA (m/m) | residual biphenol in dried washed cake (wt %) |
|---|---|---|---|---|---|
| 30 | 12 g | 12 g | Ethylene glycol | 1:1 | 0.21% |
| 31* | 12 g | 12 g + 4 g | Ethylene glycol/H₂O | 1.33:1 | 0.98% |

*Denotes comparative example

This disclosure further encompasses the following aspects.

Aspect 1: A method for purification of a biphenol tetraacid composition comprising a biphenol tetraacid of the formula

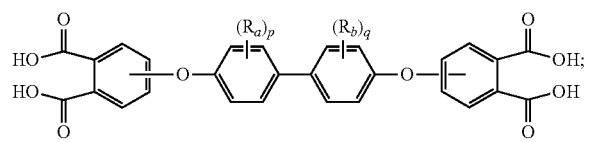

and a biphenol of the formula

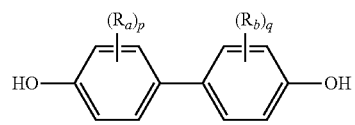

wherein in the foregoing formulas $R^a$ and $R^b$ are each independently a halogen or a monovalent $C_{1-6}$ alkyl group and p and q are each independently an integer of 0 to 4; the method comprising: contacting the biphenol tetraacid composition with a solvent comprising a $C_{1-6}$ alcohol to form a slurry comprising the biphenol tetraacid composition; and isolating a purified biphenol tetraacid from the slurry, wherein isolating the purified biphenol tetraacid comprises filtering the slurry to provide a wet cake comprising the biphenol tetraacid, and washing the wet cake with additional solvent comprising the $C_{1-6}$ alcohol, water, an organic solvent miscible with the $C_{1-6}$ alcohol, or a combination thereof.

Aspect 2: The method of aspect 1, wherein the biphenol tetraacid composition comprises 1 to 10 weight percent of the biphenol, preferably 1 to 5 weight percent, more preferably 1 to 3 weight percent, each based on the total weight of the biphenol tetraacid composition.

Aspect 3: The method of aspect 1 or 2, wherein the biphenol tetraacid composition further comprises a sodium ion, potassium ion, calcium ion, zinc ion, aluminum ion, titanium ion, iron ion, and phosphorus ion, phosphate ion, sulfate ion, chloride ion, or a combination thereof, wherein each of the sodium ion, potassium ion, calcium ion, zinc ion, aluminum ion, titanium ion, iron ion, and phosphorus ion, phosphate ion, sulfate ion, or chloride ion is present in an amount of 0 to 1700 ppm, based on the total weight of the biphenol tetraacid composition.

Aspect 4: The method of any of aspects 1 to 3, wherein p and q are each 0.

Aspect 5: The method of any of aspects 1 to 4, wherein the divalent bonds of the biphenol group of the biphenol tetraacid are in the 3,3' position, the 3,4' position, or the 4,4' position, preferably the 3,3' position.

Aspect 6: The method of any of aspects 1 to 5, wherein the biphenol tetraacid is an isomer mixture, preferably wherein 10-100 weight percent of the biphenol tetraacid have the divalent bonds of the biphenol group of the biphenol tetraacid are in the 3,3' position, more preferably wherein 90-100 weight percent of the biphenol tetraacid have the divalent bonds of the biphenol group of the biphenol tetraacid are in the 3,3' position.

Aspect 7: The method of any of aspects 1 to 6, wherein the $C_{1-6}$ alcohol comprises isopropanol, ethylene glycol, methanol, ethanol, n-propanol, butanol, pentanol, hexanol, or a combination thereof.

Aspect 8: The method of any of aspects 1 to 7, wherein the solvent further comprises water or an organic solvent miscible with the $C_{1-6}$ alcohol.

Aspect 9: The method of aspect 8, wherein the organic solvent comprises ortho-dichlorobenzene, para-dichlorobenzene, meta-dichlorobenzene, chlorobenzene, toluene, benzene, xylene, 1,2,4-trichlorobenzene, 1,3,4-trichlorobenzene, preferably ortho-dichlorobenzene.

Aspect 10: The method of any of aspects 1 to 9, wherein the purified biphenol tetraacid comprises less than 1 weight percent, preferably less than 0.7 weight percent, more preferably less than 0.2 weight percent, even more preferably less than 0.16 weight percent of the biphenol, as determined by ultra performance liquid chromatography; less than 10 ppm of sodium ions; less than 50 ppm total of sodium ions, potassium ions, calcium ions, zinc ions, aluminum ions, titanium ions, iron ions, and phosphorus ions; less than 250 ppm of sulfate ions; and less than 3,000 ppm total of phosphate ions, sulfate ions, and chloride ions.

Aspect 11: The method of any of aspects 1 to 10, further comprising agitating the slurry, preferably agitating the slurry for a time of 1 to 2 hours.

Aspect 12: The method of any of aspects 1 to 11, wherein the solvent is present in a weight ratio of solvent to biphenol tetraacid of 0.8:1 to 8:1.

Aspect 13: A biphenol tetraacid composition comprising a biphenol tetraacid of the formula

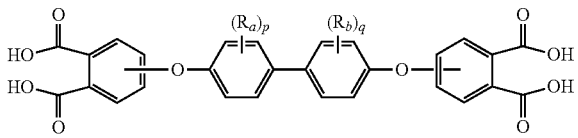

wherein $R^a$ and $R^b$ are each independently a halogen or a monovalent $C_{1-6}$ alkyl group and p and q are each independently an integer of 0 to 4; and greater than 0 to less than 1 weight percent, preferably greater than 0 to less than 0.7 weight percent, more preferably greater than 0 to less than 0.2 weight percent, even more preferably greater than 0 to less than 0.16 weight percent of the biphenol, as determined by ultra performance liquid chromatography; greater than 0 to less than 10 ppm of sodium ions; greater than 0 to less than 50 ppm total of sodium ions, potassium ions, calcium ions, zinc ions, aluminum ions, titanium ions, iron ions, and phosphorus ions; greater than 0 to less than 250 ppm of sulfate ions; and greater than 0 to less than 3,000 ppm total of phosphate ions, sulfate ions, and chloride ions.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. The term "combination thereof" as used herein includes one or more of the listed elements, and is open, allowing the presence of one or more like elements not named. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl), a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for purification of a biphenol tetraacid composition comprising
a biphenol tetraacid of the formula

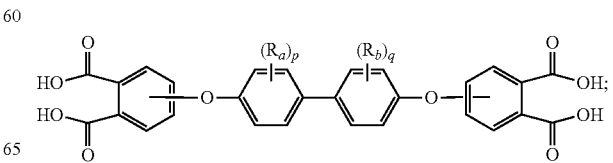

and
a biphenol of the formula

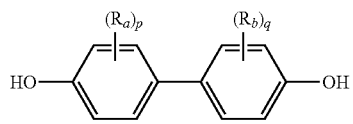

wherein in the foregoing formulas $R^a$ and $R^b$ are each independently a halogen or a monovalent $C_{1-6}$ alkyl group and p and q are each independently an integer of 0 to 4;
the method comprising:
contacting the biphenol tetraacid composition with a solvent comprising a $C_{1-6}$ alcohol to form a slurry comprising the biphenol tetraacid composition;
agitating the slurry; and
isolating a purified biphenol tetraacid from the slurry, wherein isolating the purified biphenol tetraacid comprises filtering the slurry to provide a wet cake comprising the biphenol tetraacid, and washing the wet cake with additional solvent comprising the $C_{1-6}$ alcohol, water, an organic solvent miscible with the $C_{1-6}$ alcohol, or a combination thereof.

2. The method of claim 1, wherein the biphenol tetraacid composition comprises 1 to 10 weight percent of the biphenol based on the total weight of the biphenol tetraacid composition.

3. The method of claim 1, wherein the biphenol tetraacid composition further comprises a sodium ion, potassium ion, calcium ion, zinc ion, aluminum ion, titanium ion, iron ion, and phosphorus ion, phosphate ion, sulfate ion, chloride ion, or a combination thereof, wherein each of the sodium ion, potassium ion, calcium ion, zinc ion, aluminum ion, titanium ion, iron ion, and phosphorus ion, phosphate ion, sulfate ion, or chloride ion is present in an amount of 0 to 1700 ppm, based on the total weight of the biphenol tetraacid composition.

4. The method of claim 1, wherein p and q are each 0.

5. The method of claim 1, wherein the divalent bonds of the biphenol group of the biphenol tetraacid are in the 3,3' position, the 3,4' position, or the 4,4' position, preferably the 3,3' position.

6. The method of claim 1, wherein the biphenol tetraacid is an isomer mixture.

7. The method of claim 1, wherein the $C_{1-6}$ alcohol comprises isopropanol, ethylene glycol, methanol, ethanol, «-propanol, butanol, pentanol, hexanol, or a combination thereof.

8. The method of claim 1, wherein the solvent further comprises water or an organic solvent miscible with the $C_{1-6}$ alcohol.

9. The method of claim 8, wherein the organic solvent comprises ortho-dichlorobenzene, para-dichlorobenzene, meta-dichlorobenzene, chlorobenzene, toluene, benzene, xylene, 1,2,4-trichlorobenzene, 1,3,4-trichlorobenzene.

10. The method of claim 1, wherein the purified biphenol tetraacid comprises
less than 1 weight percent of the biphenol as determined by ultra performance liquid chromatography;
less than 10 ppm of sodium ions;
less than 50 ppm total of sodium ions, potassium ions, calcium ions, zinc ions, aluminum ions, titanium ions, iron ions, and phosphorus ions;
less than 250 ppm of sulfate ions; and
less than 3,000 ppm total of phosphate ions, sulfate ions, and chloride ions.

11. The method of claim 1, wherein agitating the slurry is for a time of 1 to 5 hours.

12. The method of claim 1, wherein the solvent is present in a weight ratio of solvent to biphenol tetraacid of 0.8:1 to 8:1.

13. A biphenol tetraacid composition comprising a biphenol tetraacid of the formula

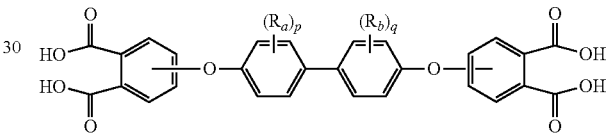

wherein $R^a$ and $R^b$ are each independently a halogen or a monovalent $C_{1-6}$ alkyl group and p and q are each independently an integer of 0 to 4; and
greater than 0 to less than 1 weight percent of the biphenol as determined by ultra performance liquid chromatography;
greater than 0 to less than 10 ppm of sodium ions;
greater than 0 to less than 50 ppm total of sodium ions, potassium ions, calcium ions, zinc ions, aluminum ions, titanium ions, iron ions, and phosphorus ions;
greater than 0 to less than 250 ppm of sulfate ions; and
greater than 0 to less than 3.000 ppm total of phosphate ions, sulfate ions, and chloride ions.

* * * * *